(12) United States Patent
Moon et al.

(10) Patent No.: US 10,485,635 B2
(45) Date of Patent: Nov. 26, 2019

(54) ORTHODONTIC APPLIANCE (71) Applicants: Won Moon, Los Angeles, CA (US); Ehab Abdelbar, Los Angeles, CA (US); Paul Kim, Diamond Bar, CA (US)

(72) Inventors: Won Moon, Los Angeles, CA (US); Ehab Abdelbar, Los Angeles, CA (US); Paul Kim, Diamond Bar, CA (US)

( * ) Notice: Subject to any disclaimer, the term of this patent is extended or adjusted under 35 U.S.C. 154(b) by 0 days.

(21) Appl. No.: 15/914,935

(22) Filed: Mar. 7, 2018

(65) Prior Publication Data

US 2019/0231482 A1    Aug. 1, 2019

Related U.S. Application Data

(60) Provisional application No. 62/624,319, filed on Jan. 31, 2018.

(51) Int. Cl.
*A61C 3/00*    (2006.01)
*A61C 7/08*    (2006.01)
*A61C 7/10*    (2006.01)

(52) U.S. Cl.
CPC . *A61C 7/08* (2013.01); *A61C 7/10* (2013.01)

(58) Field of Classification Search
CPC .................................... A61C 7/08; A61C 7/10
See application file for complete search history.

(56) References Cited

U.S. PATENT DOCUMENTS

| | | | | |
|---|---|---|---|---|
| 3,699,656 A | * | 10/1972 | Scheu | A61C 7/10 433/7 |
| 3,724,075 A | | 4/1973 | Kesling | |
| 4,253,828 A | * | 3/1981 | Coles | A61C 7/00 433/6 |
| 4,299,568 A | * | 11/1981 | Crowley | A61C 7/00 433/6 |
| 4,413,978 A | * | 11/1983 | Kurz | A61C 7/08 433/6 |
| 4,553,549 A | * | 11/1985 | Pope | A61C 7/00 433/140 |

(Continued)

OTHER PUBLICATIONS

Moon, Won; Non-Final Office Action for U.S. Appl. No. 15/914,929, filed Mar. 7, 2018, dated Jun. 28, 2018, 15 pgs.

(Continued)

*Primary Examiner* — Nicholas D Lucchesi
(74) *Attorney, Agent, or Firm* — Taylor English Duma LLP (57) ABSTRACT

Provided herein is an orthodontic frame work and methods of making and using the same. The framework is configured to be placed within a dental arch nearby a tooth or teeth of a patient in combination with an appliance via an attachment for moving the tooth or teeth, the framework being less pliable than the appliance so as to serve as an anchor or a backbone of the appliance, the appliance is effective to move a tooth or teeth from an initial position to an intermediate position or final position of the tooth or teeth according to a prescription by a treating doctor, and the attachment is via a material forming the appliance and is configured to allow the framework to exert a non-reciprocal force upon the appliance and the appliance to exert a non-reciprocal force upon the tooth or teeth.

16 Claims, 5 Drawing Sheets

(56) References Cited

U.S. PATENT DOCUMENTS

| | | | |
|---|---|---|---|
| 4,597,738 A * | 7/1986 | Sander | A61C 7/36 433/19 |
| 4,764,115 A * | 8/1988 | Willits | A61C 13/24 433/172 |
| 5,037,295 A | 8/1991 | Bergersen | |
| 5,055,039 A | 10/1991 | Abbatte et al. | |
| 5,096,416 A | 3/1992 | Hulsink | |
| 5,145,364 A | 9/1992 | Martz et al. | |
| 5,376,001 A * | 12/1994 | Tepper | A61C 7/00 433/6 |
| 5,450,807 A | 9/1995 | Moody | |
| 5,938,436 A * | 8/1999 | Shevel | A61F 5/566 128/860 |
| 5,975,893 A | 11/1999 | Chishti et al. | |
| 6,454,565 B2 * | 9/2002 | Phan | A61C 7/00 433/6 |
| 6,524,101 B1 * | 2/2003 | Phan | A61C 7/00 433/24 |
| 6,607,382 B1 * | 8/2003 | Kuo | A61C 7/08 433/216 |
| 7,328,705 B2 | 2/2008 | Abramson | |
| 7,357,633 B2 | 4/2008 | Mailyan | |
| 7,661,955 B2 | 2/2010 | Da Cruz | |
| 7,878,803 B2 | 2/2011 | Mailyan | |
| 7,955,075 B2 | 6/2011 | Mailyan | |
| 7,975,701 B2 | 7/2011 | Bergersen | |
| 8,062,031 B2 | 11/2011 | Inman | |
| 8,133,050 B2 | 3/2012 | Bergersen | |
| 8,192,196 B2 | 6/2012 | Singh | |
| 8,371,309 B2 | 2/2013 | Diers | |
| 8,414,291 B1 * | 4/2013 | Jamilian | A61C 8/0096 433/19 |
| 8,474,462 B2 | 7/2013 | Makower et al. | |
| 8,870,566 B2 | 10/2014 | Bergersen | |
| 9,011,145 B2 | 4/2015 | Hang | |
| 9,314,320 B2 * | 4/2016 | Urbanek | A61C 19/06 |
| 9,351,810 B2 | 5/2016 | Moon | |
| D777,929 S | 1/2017 | Showkatbakhsh | |
| 9,585,732 B2 | 3/2017 | Piancino | |
| 10,028,805 B2 * | 7/2018 | Tairaku | A61C 7/08 |
| 2004/0013993 A1 | 1/2004 | Ito | |
| 2004/0209218 A1 | 10/2004 | Chishti | |
| 2005/0003318 A1 | 1/2005 | Choi et al. | |
| 2005/0069834 A1 | 3/2005 | Inman | |
| 2006/0185679 A1 * | 8/2006 | Costigan | A61F 5/0006 128/848 |
| 2006/0216670 A1 * | 9/2006 | Leichtung | A61C 7/08 433/167 |
| 2007/0184398 A1 | 8/2007 | Cronauer | |
| 2008/0227048 A1 * | 9/2008 | Tjikueni | A61C 7/08 433/6 |
| 2008/0268400 A1 | 10/2008 | Moss et al. | |
| 2010/0068671 A1 | 3/2010 | Kakavand et al. | |
| 2010/0183997 A1 * | 7/2010 | Darendeliler | A61C 7/006 433/6 |
| 2011/0027743 A1 * | 2/2011 | Cinader, Jr. | A61C 7/006 433/11 |
| 2011/0236847 A1 * | 9/2011 | Hang | A61C 7/10 433/6 |
| 2011/0236849 A1 | 9/2011 | Pogorelsky | |
| 2012/0129117 A1 * | 5/2012 | McCance | A61C 7/10 433/7 |
| 2013/0089828 A1 | 4/2013 | Borovinskih | |
| 2013/0230819 A1 * | 9/2013 | Arruda | A61C 7/22 433/6 |
| 2014/0302448 A1 | 10/2014 | Cassalia | |
| 2014/0302451 A1 * | 10/2014 | Berry | A61C 7/10 433/18 |
| 2015/0125802 A1 | 5/2015 | Tal | |
| 2015/0157421 A1 | 6/2015 | Martz et al. | |
| 2015/0216627 A1 | 8/2015 | Kopelman | |
| 2015/0257856 A1 | 9/2015 | Martz et al. | |
| 2015/0265376 A1 | 9/2015 | Kopelman | |
| 2016/0081767 A1 * | 3/2016 | Metcalf | A61C 7/10 433/6 |
| 2016/0081768 A1 * | 3/2016 | Kopelman | A61C 7/10 433/6 |
| 2016/0120620 A1 * | 5/2016 | Tairaku | A61C 7/08 433/6 |
| 2016/0128803 A1 | 5/2016 | Webber et al. | |
| 2016/0310236 A1 | 10/2016 | Kopelman et al. | |
| 2017/0007367 A1 * | 1/2017 | Li | A61C 7/10 |
| 2017/0007387 A1 | 1/2017 | Cohen et al. | |
| 2017/0079747 A1 * | 3/2017 | Graf | A61C 7/002 |
| 2017/0105817 A1 | 4/2017 | Chun | |
| 2017/0156821 A1 | 6/2017 | Kopelman | |
| 2017/0156823 A1 | 6/2017 | Roein Peikar | |
| 2017/0304108 A1 * | 10/2017 | Simonetti | A61F 5/566 |
| 2017/0367791 A1 | 12/2017 | Raby | |
| 2017/0367792 A1 | 12/2017 | Raby et al. | |
| 2018/0049846 A1 | 2/2018 | Martz | |
| 2018/0055602 A1 | 3/2018 | Kopelman | |
| 2019/0046298 A1 | 2/2019 | Cinader, Jr. | |

OTHER PUBLICATIONS

Moon, Won, Restriction Requirement for U.S. Appl. No. 15/914,932, filed Mar. 7, 2018, dated May 18, 2018, 8 pgs.

Moon, Won; Non-Final Office Action for U.S. Appl. No. 15/914,932, filed Mar. 7, 2018, dated Jul. 13, 2018, 14 pgs.

Moon, Won; Advisory Action for U.S. Appl. No. 15/914,929, filed Mar. 7, 2018, dated Dec. 13, 2018, 10 pgs.

Moon, Won; Final Office Action for U.S. Appl. No. 15/914,929, filed Mar. 7, 2018, dated Oct. 3, 2018, 13 pgs.

Moon, Won; Non-Final Office Action for U.S. Appl. No. 15/914,929, filed Mar. 7, 2018, dated Jan. 10, 2019, 7 pgs.

Moon, Won; Applicant-Initiated Interview Summary for U.S. Appl. No. 15/914,932, filed Mar. 7, 2018, dated Feb. 21, 2019, 15 pgs.

Moon, Won; Final Office Action for U.S. Appl. No. 15/914,932, filed Mar. 7, 2018, dated Jan. 28, 2019, 18 pgs.

Moon, Won; Non-Final Office Action for U.S. Appl. No. 15/914,932, filed Mar. 7, 2018, dated Mar. 21, 2019, 12 pages.

Moon, Won; International Search Report and Written Opinion for PCT/US2019/015632, filed Jan. 29, 2019, dated Mar. 4, 2019, 8 pgs.

Moon, Won; International Search Report for PCT Application No. PCT/US2019/015647, filed Jan. 29, 2019, dated Feb. 28, 2019, 8 pgs.

Moon, Won, Final Office Action in U.S. Appl. No. 15/914929, filed Mar. 7, 2018, dated May 31, 2019, 18 pages.

Moon, Won; Invitation to Pay Additional Fees for serial No. PCT/US19/15639, filed Jan. 29, 2019, dated Apr. 12, 2019, 2 pgs.

Moon, Won; International Search Report and Written Opinion for PCT Application No. PCT/US19/15639, filed Jan. 29, 2019, dated Jun. 7, 2019, 11 pages.

Moon, Won; Final Office Action for U.S. Appl. No. 15/914,932, filed Mar. 7, 2018, dated Jun. 14, 2019, 15 pgs.

* cited by examiner

ORTHODONTIC APPLIANCE

FIELD OF THE INVENTION

The present invention generally relates to the field of orthodontics, and in particular to the use of orthodontic tray-type appliances, their positioning within the mouth, and methods of making and using the same.

BACKGROUND OF THE INVENTION

Traditionally, the process of orthodontics is carried out with braces and similar appliances using brackets and metal wire, in which teeth are attached to individual brackets, which are then attached to a wire. The tightness of the wire is adjusted as needed by the orthodontist; this method, which has been refined over the decades, allows for detailed control over where the brackets are pulled in what direction at how much force, and allows for easily customizable treatment as needed.

However, due to reasons such as intrusiveness in the mouth and poor aesthetics, a number of other options are currently being explored by those in the field. Among those are tray aligners, which work by placing down a thin polymer-based aligner molded to the shape of the patient's teeth; the aligner will then guide the teeth through applied force to the intended result orchestrated by digital manipulation of these teeth in sequential manner. A well-known example is Invisalign®, a polymer-based aligner based on U.S. Pat. No. 5,975,893 (Chishti et al.) and other related patents. The advantage of such aligners is that they provide less intrusion in the mouth than traditional braces, allowing for the patient's further comfort in day-to-day tasks such as eating, brushing, and flossing.

A weakness of this method is that, by itself, it cannot effectively account for the necessary differential force that must be applied to different teeth for certain tooth movements. Conventional orthodontic methods generally require a designated anchor point to use as a basis from where force is exerted, thus allowing for direct control over the direction and amount of force applied on the teeth. However, with tray aligners as described above, generated force is entirely dependent on reciprocal anchorage, meaning that a group of teeth is pulled, pushed, torqued and rotated against adjacent groups of teeth. As such, some unwanted movement from adjacent teeth (anchor teeth) may be inevitable and should be accounted for during treatment. Additionally, the effectiveness of force application is dependent on the quality of anchor teeth, which may not be adequate for certain tooth movements.

Bodily tooth movement during the space closure in extraction cases, torque control, anterior intrusion, rotation of posterior teeth and root movements are known to be challenging with the traditional clear aligner appliances (e.g., the ones described in U.S. Pat. No. 5,975,893). Aligners such as Invisalign® are created by vacuum-fitting a sheet of polymer over a mold of the teeth, which results in the polymer having a roughly even thickness over the aligner. Thus, tooth movement is largely guided by reciprocal force between the teeth towards an overall goal, and may result in unintended side effects, such as lack of proper force magnitudes and incorrect direction due to multiple components exerting force onto each other.

Therefore, there is a need for aligners that overcome the aforementioned short-comings of the clear aligner.

Therefore, the embodiments described below address the above-identified issues and needs.

SUMMARY OF THE INVENTION

In one aspect of the present invention, it is provided an orthodontic framework capable of being placed within the dental arch nearby a tooth or teeth of a patient in combination with an appliance via an attachment for moving the tooth or teeth, wherein the framework is less pliable than the appliance such that the framework serves as the anchor of the appliance, wherein the appliance is effective to move a tooth or teeth from an initial position to an intermediate position or final position of the tooth or teeth according to a prescription by a treating doctor, and wherein the attachment is via a material forming the appliance in a manner that the framework is capable of exerting a non-reciprocal force upon the appliance and the appliance is capable of exerting a non-reciprocal force upon teeth using the framework as backbone or anchor.

In some embodiments the framework is ACTIVE meaning it can exert forces on specific teeth to cause their movement.

In some embodiments of the invention framework, optionally in combination with any of the various embodiments disclosed herein, the framework is capable of being placed on the lingual or labial positions of various distance from the teeth and gum of the patient.

In some embodiments of the invention framework, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention framework, optionally in combination with any of the various embodiments disclosed herein, the attachment is through mechanical interlocking, adhesion or chemical bonding.

In some embodiments of the invention framework, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention framework, optionally in combination with any of the various embodiments disclosed herein, the framework is formed from a material of sufficient mechanical strength which is less pliable than the polymer material forming the appliance so as to act as a base for the appliance formed from the more pliable polymer.

In some embodiments of the invention framework, optionally in combination with any of the various embodiments disclosed herein, the appliance is an elastic appliance.

In another aspect of the present invention, it is provided an orthodontic tray device, comprising an orthodontic framework and an appliance comprising a polymer material, wherein the orthodontic framework is capable of being placed within the dental arch nearby a tooth or teeth of a patient in combination with an appliance via an attachment for moving the tooth or teeth, wherein the framework is less pliable than the appliance such that the framework serves as the anchor of the appliance, wherein the appliance is effective to move a tooth or teeth from an initial position to an intermediate position or final position of the tooth or teeth according to a prescription by a treating doctor, and wherein the attachment is via a material forming the appliance in a manner that the framework is capable of exerting a non-reciprocal force upon the appliance and the appliance is capable of exerting a non-reciprocal force upon teeth using the framework as backbone or anchor.

In some embodiments of the invention tray device, optionally in combination with any of the various embodiments disclosed herein, the framework is capable of being placed on the lingual or labial positions of various distance from the teeth and gum of the patient.

In some embodiments of the invention tray device, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention tray device, optionally in combination with any of the various embodiments disclosed herein, the attachment is through mechanical interlocking, adhesion or chemical bonding.

In some embodiments of the invention tray device, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention tray device, optionally in combination with any of the various embodiments disclosed herein, the orthodontic framework is formed from a material of sufficient mechanical strength which is less pliable than the polymer material forming the appliance so as to act as a base for the appliance formed from the more pliable polymer.

In some embodiments of the invention tray device, optionally in combination with any of the various embodiments disclosed herein, the appliance is an elastic appliance.

In some embodiments of the invention tray device, optionally in combination with any of the various embodiments disclosed herein, the framework comprises two moieties for placing on gum of the patient, one moiety for being placed on the gum inside the dental arch, and the other moiety for being placed on the gum outside the dental arch, both moieties of the framework capable of locking between the teeth or behind the teeth or behind the teeth or behind the teeth.

In some embodiments of the invention tray device, optionally in combination with any of the various embodiments disclosed herein, the two moieties join each other at the ends the two moieties, forming a loop, and/or a middle point or middle points, where such joining at a middle point or middle points is(are) between adjacent teeth such that it (they) would not interfere with use of the teeth.

In some embodiments of the invention tray device, optionally in combination with any of the various embodiments disclosed herein, the framework comprises a single moiety for placing on gum of the patient, either inside the dental arch or outside the dental arch, the moiety capable of locking between the teeth or behind the teeth or behind the teeth or behind the teeth.

In a further aspect of the present invention, it is provided a method of fabrication, which method comprising:

creating a tooth model of a patient, and forming the orthodontic framework, wherein the orthodontic framework is capable of being placed within the dental arch nearby a tooth or teeth of a patient in combination with an appliance via an attachment for moving the tooth or teeth, wherein the framework is less pliable than the appliance such that the framework serves as the anchor of the appliance, wherein the appliance is effective to move a tooth or teeth from an initial position to an intermediate position or final position of the tooth or teeth according to a prescription by a treating doctor, and wherein the attachment is via a material forming the appliance in a manner that the framework is capable of exerting a non-reciprocal force upon the appliance and the appliance is capable of exerting a non-reciprocal force upon teeth using the framework as backbone or anchor.

In some embodiments of the invention method, optionally in combination with any of the various embodiments disclosed herein, the framework is capable of being placed on the lingual or labial positions of various distance from the teeth and gum of the patient.

In some embodiments of the invention method, optionally in combination with any of the various embodiments disclosed herein, the method further comprising providing the appliance for moving the tooth or teeth.

In some embodiments of the invention method, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention method, optionally in combination with any of the various embodiments disclosed herein, the attachment is through mechanical interlocking, adhesion or chemical bonding.

In some embodiments of the invention method, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention method, optionally in combination with any of the various embodiments disclosed herein, the orthodontic framework is formed from a material of sufficient mechanical strength which is less pliable than the polymer material forming the appliance so as to act as a base for the appliance formed from the more pliable polymer.

In some embodiments of the invention method, optionally in combination with any of the various embodiments disclosed herein, the appliance is an elastic appliance.

In a further aspect of the present invention, it is provided a method of orthodontic treatment, comprising creating a tooth model of a patient, forming the orthodontic framework, and placing the orthodontic framework within the dental arch nearby a tooth or teeth of a patient, wherein the framework is in combination with an appliance via an attachment for moving the tooth or teeth, wherein the framework is less pliable than the appliance such that the framework serves as the anchor of the appliance, wherein the appliance is effective to move a tooth or teeth from an initial position to an intermediate position or final position of the tooth or teeth according to a prescription by a treating doctor, and wherein the attachment is via a material forming the appliance in a manner that the framework is capable of exerting a non-reciprocal force upon the appliance and the appliance is capable of exerting a non-reciprocal force upon teeth using the framework as backbone or anchor.

In some embodiments of the invention method, optionally in combination with any of the various embodiments disclosed herein, the framework is capable of being placed on the lingual or labial positions of various distance from the teeth and gum of the patient.

In some embodiments of the invention method, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention method, optionally in combination with any of the various embodiments disclosed herein, the attachment is through mechanical interlocking, adhesion or chemical bonding.

In some embodiments of the invention method, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention method, optionally in combination with any of the various embodiments disclosed herein, the orthodontic framework is formed from a material of sufficient mechanical strength which is less pliable than the polymer material forming the appliance so as to act as a base for the appliance formed from the more pliable polymer.

In some embodiments of the invention method, optionally in combination with any of the various embodiments disclosed herein, the appliance is an elastic appliance.

DETAILED DESCRIPTION OF THE INVENTION

Definitions

As used herein, a "tray-type aligner" is defined as a clear tray that covers the teeth and guides one or more of the teeth to move from its/their original position(s) to the final position(s) over a period of time as prescribed by a treating doctor, who is also referred to as an "orthodontic doctor" or an "orthodontist".

As used herein, the term "anchorage" refers to the resistance used to overcome the reaction of an applied force. According to Newton's third law of motion, to every action there is an equal and opposite reaction.

As used herein, the term "reciprocal force" refers to a force applied by an orthodontic anchorage in which the resistance of one or more teeth and their adnexa is used to move one or more opposing teeth and their adnexa; and in this context, such an anchorage is referred to as a "reciprocal anchorage" such as the anchorage used in conventional Invisalign™ aligners.

As used herein, the term "non-reciprocal force" refers to a force applied by an orthodontic anchorage of an anchoring point that is independent of a tooth or teeth so as to avoid reciprocity of tooth movement caused by a conventional plastic aligner such as Invisalign™. Such a "non-reciprocal force" can also be referred to as an "independent, non-reciprocal force."

As used herein, the term "original position" of tooth or teeth refers to the position of the tooth or teeth of the target of treatment prior to the treatment using the appliance of invention; and the term "final position" refers to position of such tooth or teeth at the conclusion time point of an orthodontic treatment course prescribed by a treating doctor; and the term "intermediate position" refers to any position between the original position and the final position of the tooth or teeth of the target of treatment prescribed by a treating doctor.

As used herein, the term "appliance" or "aligner", which is used interchangeably herein, refers to an orthodontic device for moving a tooth or teeth according to a prescription by a treating doctor. Clear orthodontic appliances refer to those made from a plastic material, which is generally a polyester material. Such clear appliances are exemplified by Invisalign® aligners. The Invisalign® aligners, and methods of making and using the same, are described in general in U.S. Pat. Nos. 6,450,807, and 5,975,893, the teachings of which are incorporated herein by reference in their entirety.

As used herein, the term "elastic appliance" refers to an orthodontic appliance capable of being stretched to a substantially higher degree than traditional polymer based clear aligners, such as the Invisalign® aligners. Examples of such elastic appliance are described in the co-pending patent application U.S. Provisional Patent Application Ser. No. 62/624,281, entitled "Elastic Orthodontic Appliance", filed on Jan. 31, 2018, the teaching of which is incorporated herein in its entirety by reference.

As used herein, the term "a tooth model" refers to a conventional or digital tooth model.

As used herein, the term "framework" is used interchangeably with the term "backbone".

Orthodontic Framework

In order to remedy this problem, rigid frameworks can be incorporated into the aligners as a backbone (non-reciprocal anchorage), which in turn will eliminate the above problems associated with the reciprocal anchorage. Such a framework would be placed in strategic locations where the aligner can be attached to, allowing the aligner to apply necessary force on the teeth in the desired direction, at the desired moment, and with the desired amount of force without negatively impacting adjacent teeth, simply by using the framework as a backbone.

Therefore, in one aspect of the present invention, it is provided an orthodontic framework capable of being placed within the dental arch nearby a tooth or teeth of a patient in combination with an appliance via an attachment for moving the tooth or teeth,
  wherein the attachment is via a material forming the appliance in a manner that the framework is capable of exerting a non-reciprocal force upon the appliance and the appliance is capable of exerting a non-reciprocal force upon teeth using the framework as backbone or anchor,
  wherein the framework is less pliable than the appliance such that the framework serves as the anchor of the appliance, and
  wherein the appliance is effective to move a tooth or teeth from an initial position to an intermediate position or final position of the tooth or teeth according to a prescription by a treating doctor.

In some embodiments of the invention framework, optionally in combination with any of the various embodiments disclosed herein, the framework is capable of being placed on the lingual or labial positions of various distance from the teeth and gum of the patient.

In some embodiments of the invention framework, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention framework, optionally in combination with any of the various embodiments disclosed herein, the attachment is through mechanical interlocking, adhesion or chemical bonding.

In some embodiments of the invention framework, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention framework, optionally in combination with any of the various embodiments disclosed herein, the framework is formed from a material of sufficient mechanical strength which is less pliable than the polymer material forming the appliance so as to act as a base for the appliance formed from the more pliable polymer. In some embodiments, the framework itself is of a design capable of being activated to move teeth.

In some embodiments of the invention framework, optionally in combination with any of the various embodiments disclosed herein, the appliance is an elastic appliance.

Figure 1:
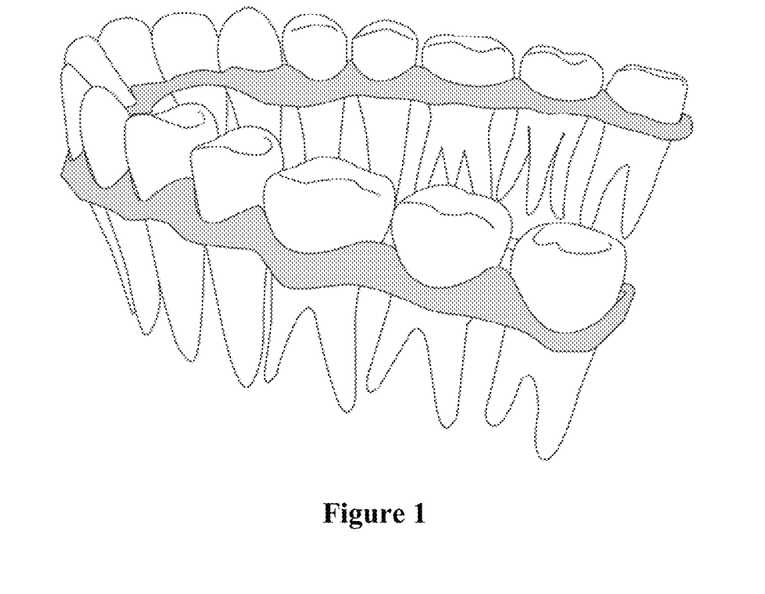
FIG. 1 is an image of an embodiment of invention framework locked in between the teeth and on the gum, left (outside the dental arch): a moiety of invention framework locked on the side of gum outside the dental arch; right (inside the dental arch): another moiety of invention framework locked on the side of gum inside the dental arch, the two moieties joining each other at the ends the two moieties.
Figure 2:
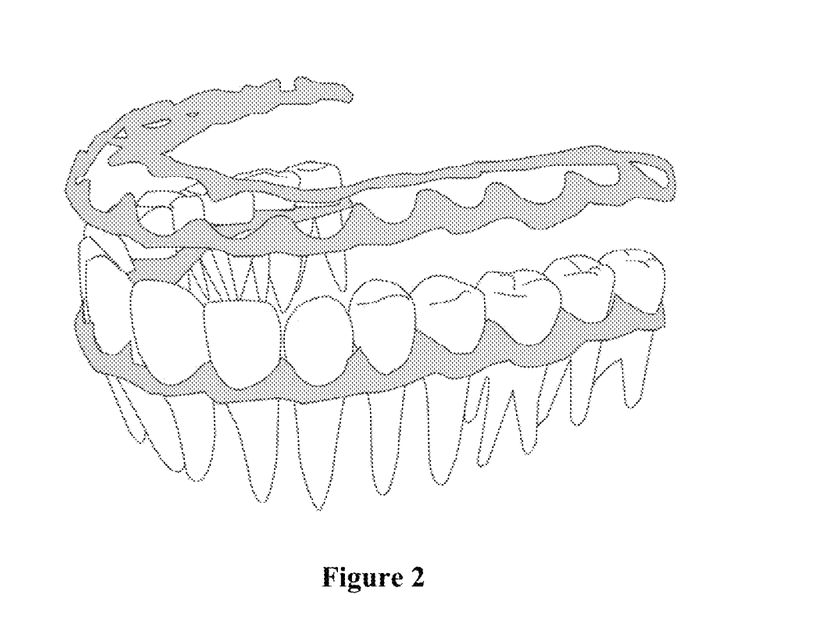
FIG. 2 shows an image of an embodiment of invention framework prior to being placed on the gum and locking between the teeth; left (outside the dental arch): a moiety of invention framework locked on the side of gum outside the dental arch; right (inside the dental arch): another moiety of invention framework locked on the side of gum inside the dental arch, the two moieties joining each other at the ends the two moieties.

In some embodiments of the invention tray device, optionally in combination with any of the various embodiments disclosed herein, the framework comprises two moieties for placing on gum of the patient, one moiety for being placed on the gum inside the dental arch, and the other moiety for being placed on the gum outside the dental arch, both moieties of the framework capable of locking between the teeth or behind the teeth or behind the teeth or behind the teeth (FIGS. 1-2).

In some embodiments of the invention tray device, optionally in combination with any of the various embodiments disclosed herein, the two moieties join each other at the ends the two moieties, forming a loop, and/or a middle point or middle points, where such joining at a middle point or middle points is(are) between adjacent teeth such that it (they) would not interfere with use of the teeth (FIGS. 1-2).

In some embodiments of the invention tray device, optionally in combination with any of the various embodiments disclosed herein, the framework comprises a single moiety for placing on gum of the patient, either inside the dental arch or outside the dental arch, the moiety capable of locking between the teeth or behind the teeth or behind the teeth or behind the teeth (FIGS. 3-6).

The invention framework serves as independent anchorage, in contrast to reciprocal anchorage used in traditional setups and allows the aligner to apply complex force vectors to a specific tooth, something that is often difficult to achieve with traditional approach. This intricate force applied to teeth on an individual basis is possible by using the framework as a backbone. The framework of invention serving as independent anchorage minimizes the undesirable reciprocal forces among the teeth, which allows for more effective, efficient, and precise tooth movements, and thus, the framework of invention is advantageous over conventional orthodontic devices having no independent anchorage.

Note that the framework's location as provided here is an example, and the framework itself can be placed in any location such as long as it is attached to the aligner in some way.

The advantage of such a mechanism is that it can be easily adjusted by the orthodontist as needed, allowing for more flexible treatment, but may have lower stability than that of the chemically bonded version; thus, the orthodontist can choose which method works best or is more financially feasible for the patient's needs FIG. 1 is an image of an embodiment of invention framework locked in between the teeth and on the gum, left (outside the dental arch): a moiety of invention framework locked on the side of gum outside the dental arch; right (inside the dental arch): another moiety of invention framework locked on the side of gum inside the dental arch, the two moieties joining each other at the ends the two moieties.

FIG. 2 shows an image of an embodiment of invention framework prior to being placed on the gum and locking between the teeth; left (outside the dental arch): a moiety of invention framework locked on the side of gum outside the dental arch; right (inside the dental arch): another moiety of invention framework locked on the side of gum inside the dental arch, the two moieties joining each other at the ends the two moieties.

Figure 3:
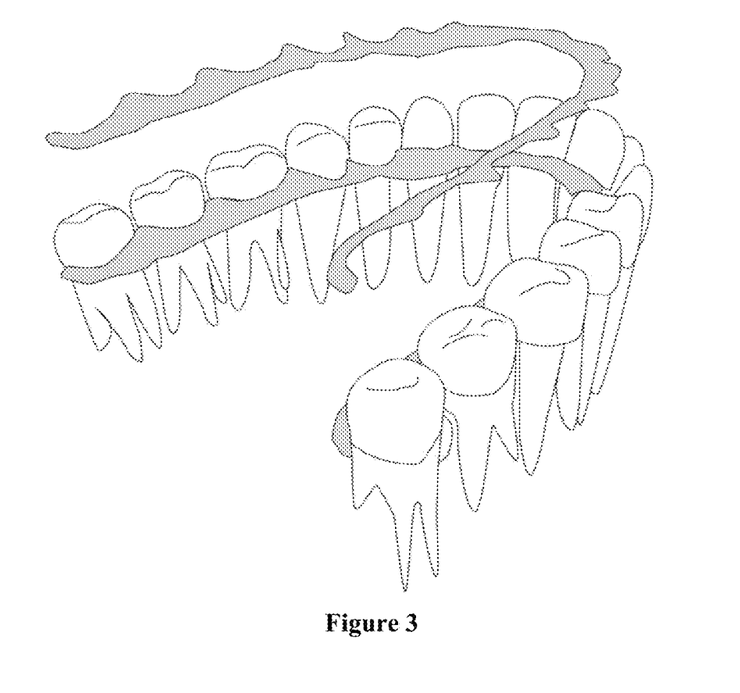
FIG. 3 is an image of an embodiment of invention framework to be placed on the gum inside the dental arch, the moiety capable of locking between the teeth or behind the teeth or behind the teeth or behind the teeth.

FIG. 3 is an image of an embodiment of invention framework to be placed on the gum inside the dental arch, the moiety capable of locking between the teeth or behind the teeth or behind the teeth or behind the teeth.

Figure 4:
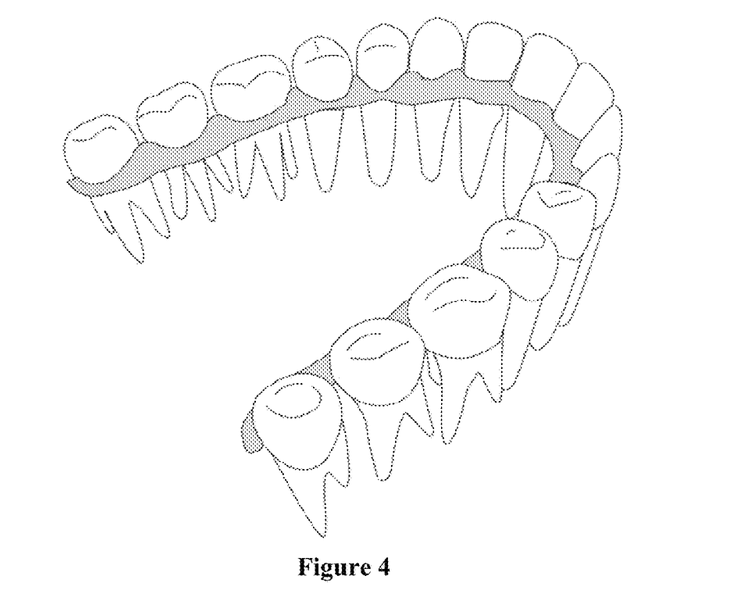
FIG. 4 is an image of an embodiment of invention framework being placed on the gum inside the dental arch and locked between the teeth.

FIG. 4 is an image of an embodiment of invention framework being placed on the gum inside the dental arch and locked between the teeth.

Figure 5:
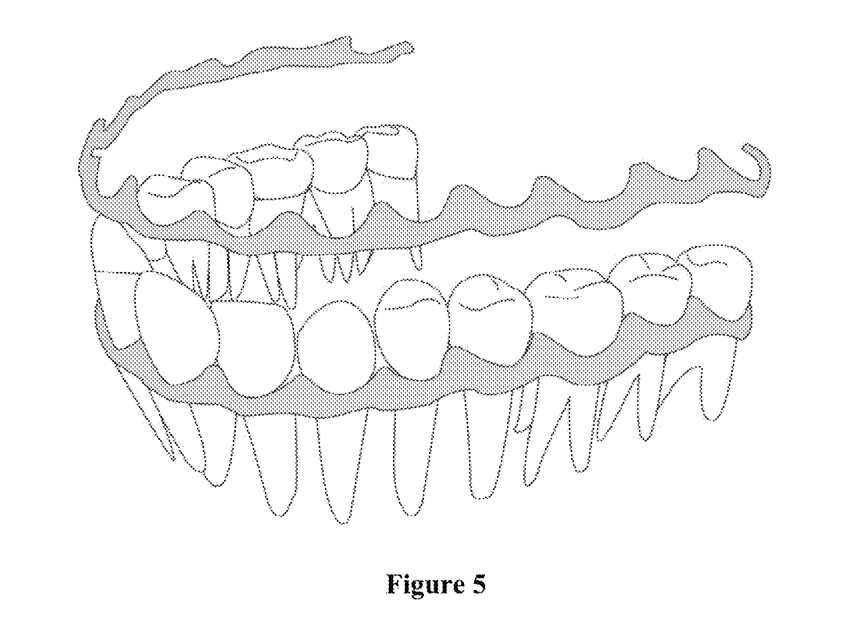
FIG. 5 is an image of an embodiment of invention framework to be placed on the gum outside the dental arch, the moiety capable of locking between the teeth or behind the teeth or behind the teeth or behind the teeth.

FIG. 5 is an image of an embodiment of invention framework to be placed on the gum outside the dental arch, the moiety capable of locking between the teeth or behind the teeth or behind the teeth or behind the teeth.

Figure 6:
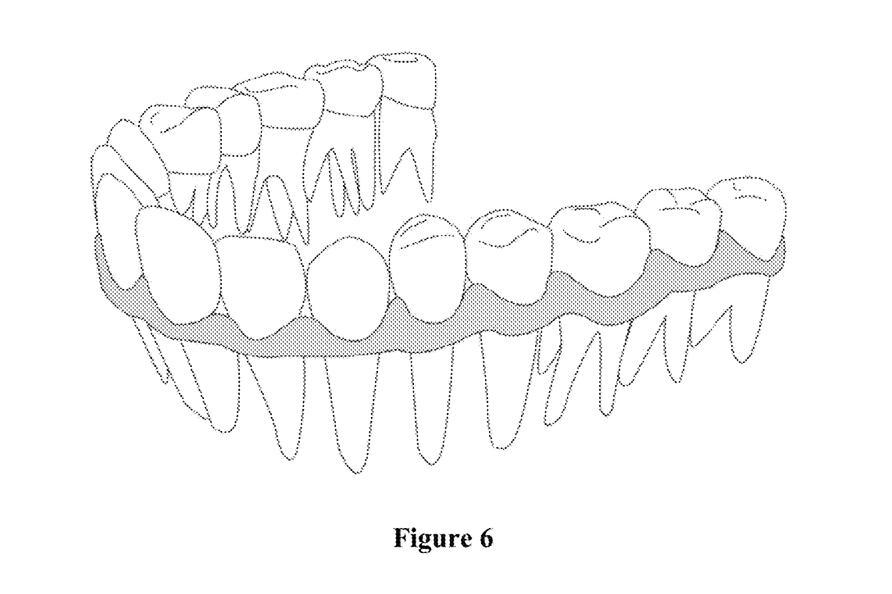
FIG. 6 is an image of an embodiment of invention framework being placed on the gum outside the dental arch and locked between the teeth.

FIG. 6 is an image of an embodiment of invention framework being placed on the gum outside the dental arch and locked between the teeth.

Figure 7:
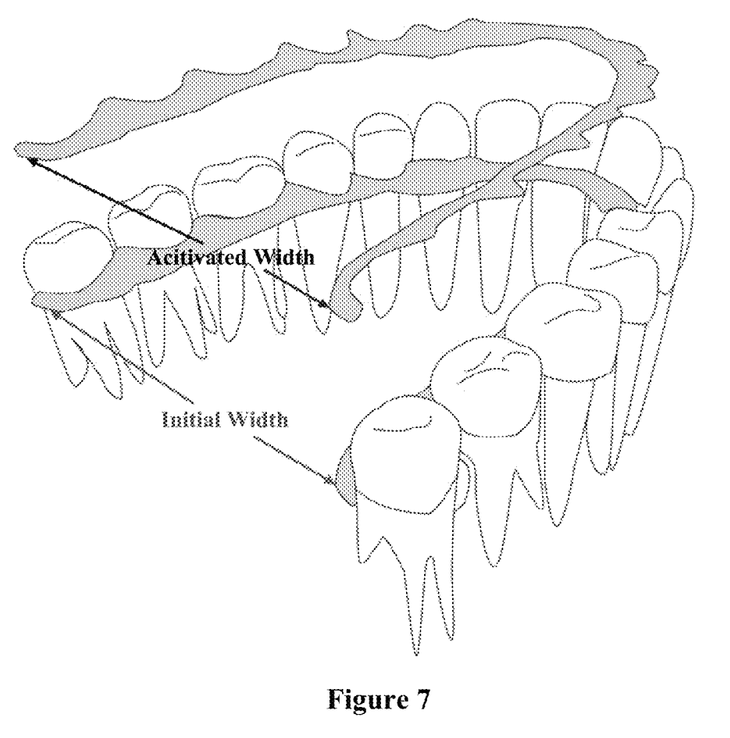
FIG. 7 is an image of an embodiment of invention framework where an invention framework is used to expand or constrict the dental arch.

FIG. 7 is an image of an embodiment of invention framework where an invention framework is used to expand or constrict the dental arch. The framework can be made to have an activated width that is smaller or larger than that of the dental arch. A larger activated width of the invention framework can be applied to the patient or user according to the various embodiments described herein to expand the dental arch of the patient or user. Conversely, a smaller activated width of the invention framework can be applied to the patient or user according to the various embodiments described herein to constrict the dental arch of the patient or user.

However, it is important that the new backbone does not obstruct the ability of the appliance to do its job, and it must also be able to allow for patient comfort. Therefore, the backbone must be placed in some area that will not get in the way of the path of the teeth when biting down, nor may it allow for interference in the forces applied to the teeth.

Orthodontic Appliances

By using the framework, it is possible to make tray aligners and other alternative methods of orthodontics and fine-tune them as desired to create effective and expedient results, as well as customize treatment necessities more deeply in order to fit the financial needs of the patient. In addition, this can lead to the development of further research revolving around tray-type appliances, allowing for the exploration of more alternative methods of orthodontics, more options for the patient, and more ways to deliver precise results.

The appliance itself can be used alongside with a polymer-based appliance like Invisalign® appliances, e.g., those described in general in U.S. Pat. Nos. 6,450,807, and 5,975,893, or any other appliance made to guide tooth movement through force, serving as a backbone for the ultimate desired result. It can also be made of any material in itself, provided that it is less pliable than the rest of the appliance by default as it stands as an anchor point.

Attachment

The term "attachment" as used herein, refers to attachment of the invention framework to an orthodontic appliance for moving a tooth or teeth, which is achieved in a way that allows the framework of invention to be able to exert sufficient force to the orthodontic appliance so as to allow the framework of invention to serve as anchorage of the appliance. As anchorage of the orthodontic appliance, the invention framework and the attachment, each must be less flexible than the orthodontic appliance.

As used herein, the term "permanent attachment" refers to attaching a framework of invention to an orthodontic appliance to form a bonding between the invention framework and the appliance, where the bonding is such that it shall remain intact without using a force that will cause structural damage to the framework of invention and/or the appliance. A permanent attachment can be broken by, for example breaking the attachment using a force, for example, cutting (e.g., by scissors, by a knife, or by laser), using a solvent to dissolve the attachment, or sometimes using heat to melt or burn off the attachment.

As used herein, the term "semi-permanent attachment" refers to attaching a framework of invention to an orthodontic appliance to form a bonding between the invention framework and the appliance, where the bonding is such that—

1) it shall remain intact using a force at a level of the net value of the force of the invention framework exerting upon the appliance, the aligning force from the appliance exerted upon the attachment, and the force generated from normal use of teeth, e.g., biting with or without food, and 2) it will break using a force higher than a force as described in 1), but will not cause structural damage to the framework of invention and/or the appliance.

As used herein, the term "removable attachment" refers to attaching a framework of invention to an orthodontic appliance by physical means without forming a bonding between the invention framework and the appliance. Such removable attachment shall remain intact using a force at a level of the net value of the force of the invention framework exerting upon the appliance, the aligning force from the appliance exerted upon the attachment, and the force generated from normal use of teeth, e.g., biting with or without food.

The attachment can be made through methods including, but not limited to mechanical interlocking, adhesion, or chemical bonding; these methods can be permanent, semi-permanent, or removable, allowing the orthodontist to choose which works best for them based on their production needs or necessity to make large adjustments during treatment. The attachment can also be made of any material, provided it is sturdy enough to act as a base for the more pliable polymer to act on.

Orthodontic Tray Device

In another aspect of the present invention, it is provided an orthodontic tray device, comprising an orthodontic framework and an appliance comprising a polymer material, wherein the orthodontic framework is capable of being placed within the dental arch nearby a tooth or teeth of a patient for attachment to an appliance for moving the tooth or teeth, wherein the attachment is via a material forming the appliance in a manner that the framework is capable of exerting a non-reciprocal force upon the appliance and the appliance is capable of exerting a non-reciprocal force upon teeth using the framework as backbone or anchor, wherein the framework is less pliable than the appliance such that the framework serves as the anchor of the appliance, and wherein the appliance is effective to move a tooth or teeth from an initial position to an intermediate position or final position of the tooth or teeth according to a prescription by a treating doctor.

In some embodiments of the invention tray device, optionally in combination with any of the various embodiments disclosed herein, the framework is capable of being placed on the lingual or labial positions of various distance from the teeth and gum of the patient.

In some embodiments of the invention tray device, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention tray device, optionally in combination with any of the various embodiments disclosed herein, the attachment is through mechanical interlocking, adhesion or chemical bonding.

In some embodiments of the invention tray device, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention tray device, optionally in combination with any of the various embodiments disclosed herein, the orthodontic framework is formed from a material of sufficient mechanical strength which is less pliable than the polymer material forming the appliance so as to act as a base for the appliance formed from the more pliable polymer. In some embodiments, the framework itself is of a design capable of being activated to move teeth.

In some embodiments of the invention tray device, optionally in combination with any of the various embodiments disclosed herein, the appliance is an elastic appliance.

Method of Fabrication

In a further aspect of the present invention, it is provided a method of fabrication, which method comprising:
  creating a tooth model of a patient, and
  forming the orthodontic framework,
    wherein the orthodontic framework is capable of being placed within the dental arch nearby a tooth or teeth of a patient for attachment to an appliance for moving the tooth or teeth,
    wherein the attachment is via a material forming the appliance in a manner that the framework is capable of exerting a non-reciprocal force upon the appliance and the appliance is capable of exerting a non-reciprocal force upon teeth using the framework as backbone or anchor,
    wherein the framework is less pliable than the appliance such that the framework serves as the anchor of the appliance, and
    wherein the appliance is effective to move a tooth or teeth from an initial position to an intermediate position or final position of the tooth or teeth according to a prescription by a treating doctor.

In some embodiments of the invention method, optionally in combination with any of the various embodiments disclosed herein, the framework is capable of being placed on the lingual or labial positions of various distance from the teeth and gum of the patient.

In some embodiments of the invention method, optionally in combination with any of the various embodiments disclosed herein, the method further comprising providing the appliance for moving the tooth or teeth.

In some embodiments of the invention method, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention method, optionally in combination with any of the various embodiments disclosed herein, the attachment is through mechanical interlocking, adhesion or chemical bonding.

In some embodiments of the invention method, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention method, optionally in combination with any of the various embodiments disclosed herein, the orthodontic framework is formed from a material of sufficient mechanical strength which is less pliable than the polymer material forming the appliance so as to act as a base for the appliance formed from the more pliable polymer. In some embodiments, the framework itself is of a design capable of being activated to move teeth.

In some embodiments of the invention method, optionally in combination with any of the various embodiments disclosed herein, the appliance is an elastic appliance.

Methods of computer aided fabrication of orthodontic appliances are well documented in the art. Examples of such methods are described in U.S. Pat. Nos. 6,450,807, and 5,975,893, the teachings of which are incorporated herein by reference in their entirety.

Method of Use

In a further aspect of the present invention, it is provided a method of orthodontic treatment, comprising:
  creating a tooth model of a patient;
  forming the orthodontic framework; and
  placing the orthodontic framework within the dental arch nearby a tooth or teeth of a patient for attachment to an appliance for moving the tooth or teeth:
    wherein the attachment is via a material forming the appliance in a manner that the framework is capable of exerting a non-reciprocal force upon the appliance and the appliance is capable of exerting a non-reciprocal force upon teeth using the framework as backbone or anchor,
    wherein the framework is less pliable than the appliance such that the framework serves as the anchor of the appliance and
    wherein the appliance is effective to move a tooth or teeth from an initial position to an intermediate position or final position of the tooth or teeth according to a prescription by a treating doctor.

In some embodiments of the invention method, optionally in combination with any of the various embodiments disclosed herein, the framework is capable of being placed on the lingual or labial positions of various distance from the teeth and gum of the patient.

In some embodiments of the invention method, optionally in combination with any of the various embodiments disclosed herein, the appliance is a polymer-based appliance or an appliance of another type guiding tooth movement through force, wherein the framework serves as a backbone to facilitate an orthodontic treatment prescribed by a treating document to cause the tooth to arrive at the desired result prescribed by the treating doctor.

In some embodiments of the invention method, optionally in combination with any of the various embodiments disclosed herein, the attachment is through mechanical interlocking, adhesion or chemical bonding.

In some embodiments of the invention method, optionally in combination with any of the various embodiments disclosed herein, the attachment is a permanent attachment, semi-permanent attachment or removable attachment to cause the tooth to move at a tooth position adjustment prescribed by a treating doctor.

In some embodiments of the invention method, optionally in combination with any of the various embodiments disclosed herein, the orthodontic framework is formed from a material of sufficient mechanical strength which is less pliable than the polymer material forming the appliance so as to act as a base for the appliance formed from the more pliable polymer. In some embodiments, the framework itself is of a design capable of being activated to move teeth.

In some embodiments of the invention method, optionally in combination with any of the various embodiments disclosed herein, the appliance is an elastic appliance.

The following examples illustrate rather than limit the embodiments of the present invention.

FIGS. 1-7 show various embodiment appliances of invention, which can be readily formed by the methods described herein.

Figure 8A:
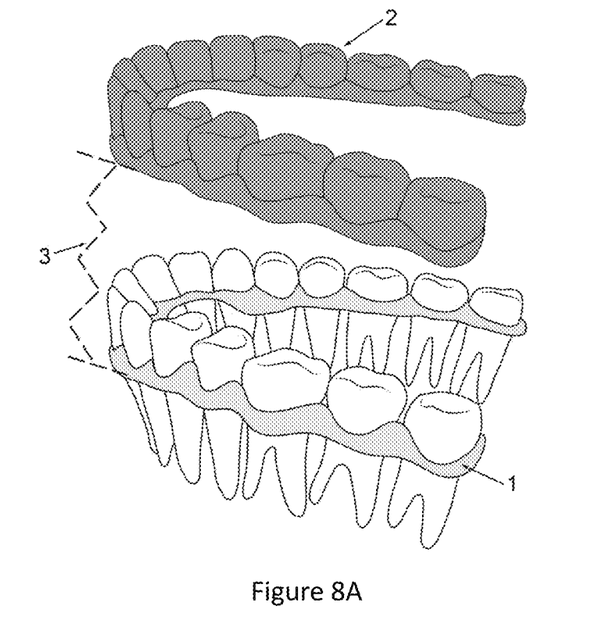
FIGS. 8A-8B illustrate an embodiment of the invention frame.
Figure 8B:
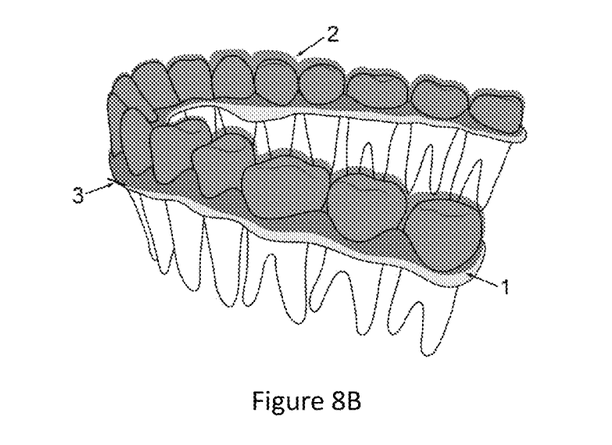

FIGS. 8A-8B illustrate an embodiment of the invention frame. In FIG. 8A, frame 1 is placed on a lower dental arch, with is connected to an orthodontic Appliance 2 via an attachment 3, the dash line denoting attachment 3 being indicative that the way of attachment and place of attachment on the framework and the corresponding place on the appliance are open. FIG. 8B shows appliance 2 is placed onto the dental arch and framework 1 and appliance is attached to appliance 2 (attachment 3 not shown).

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The teachings of the references, including patents and patent related documents, cited herein are incorporated herein in their entirety to the extent not inconsistent with the teachings herein.

We claim:

1. A combination of an orthodontic framework and an appliance, the orthodontic framework configured to be placed within a dental arch nearby a tooth or teeth of a patient in combination with the appliance via an attachment for moving the tooth or teeth,
   wherein the framework is of an open and flat structure and formed of a material comprising a polymer and is of a sufficient mechanical strength such that the framework serves as a backbone or an anchor of the appliance,
   wherein the appliance is a tray-type appliance and is formed of a polymer material and is effective to move a tooth or teeth from an initial position to an intermediate position or final position of the tooth or teeth according to a prescription by a treating doctor, and
   wherein the attachment is via the polymer material forming the appliance and is configured to allow the framework to exert a non-reciprocal force upon the appliance and the appliance to exert a non-reciprocal force upon the tooth or teeth.

2. The combination according to claim 1, wherein the framework is configured to be placed on the lingual or labial positions of various distances from the teeth and gum of the patient.

3. The combination according to claim 1, wherein the appliance guides tooth movement through force, and wherein the framework facilitates an orthodontic treatment prescribed by a treating doctor to cause the tooth or teeth to arrive at the desired result prescribed by the treating doctor.

4. The combination according to claim 1, wherein the attachment is achieved through mechanical interlocking, adhesion or chemical bonding.

5. The combination according to claim 1, wherein the attachment is a permanent attachment, semi-permanent attachment or removable attachment and is adapted to cause the tooth or teeth to move at a tooth position adjustment prescribed by a treating doctor.

6. The combination according to claim 5, wherein the appliance is formed of an elastic polymer.

7. The combination according to claim 1, wherein the appliance is formed of an elastic polymer.

8. The combination according to claim 1, wherein the framework comprises two moieties for placing on gums of the patient, one moiety configured to be placed on the gum inside the dental arch, and the other moiety configured to be placed on the gum outside the dental arch, the two moieties being configured to lock between the teeth or behind the teeth.

9. The combination according to claim 1, wherein the framework comprises a single moiety configured to be placed on the gum of the patient, either inside the dental arch or outside the dental arch, the moiety being configured to lock between the teeth or behind the teeth.

10. The combination according to claim 1, wherein the framework is of a design capable of being activated to move the tooth or teeth.

11. A method of orthodontic treatment, comprising:
   creating a tooth model of a patient,
   forming an orthodontic framework, and
   placing the orthodontic framework within the dental arch nearby a tooth or teeth of a patient,
   wherein the framework is in combination with an appliance via an attachment for moving the tooth or teeth,
   wherein the framework is of an open and flat structure and formed of a material comprising a polymer and is of a sufficient mechanical strength such that the framework serves as a backbone or an anchor of the appliance,
   wherein the appliance is a tray-type appliance and is formed of a polymer material and is effective to move a tooth or teeth from an initial position to an intermediate position or final position of the tooth or teeth according to a prescription by a treating doctor, and
   wherein the attachment is via the polymer material forming the appliance and is configured to allow the framework to exert a non-reciprocal force upon the appliance and the appliance to exert a non-reciprocal force upon the tooth or teeth.

12. The method according to claim 11, wherein the framework is configured to be placed on the lingual or labial positions of various distances from the teeth and gum of the patient.

13. The method according to claim 11, wherein the appliance guides tooth movement through force, and wherein the framework facilitates an orthodontic treatment prescribed by a treating doctor to cause the tooth or teeth to arrive at the desired result prescribed by the treating doctor.

14. The method according to claim 11, wherein the attachment is achieved through mechanical interlocking, adhesion or chemical bonding.

15. The method according to claim 11, wherein the attachment is a permanent attachment, semi-permanent attachment or removable attachment and is adapted to cause the tooth or teeth to move at a tooth position adjustment prescribed by the treating doctor.

16. The method according to claim 11, wherein the appliance is formed of an elastic polymer.

* * * * *